(12) United States Patent
Shaw

(10) Patent No.: US 8,516,108 B2
(45) Date of Patent: Aug. 20, 2013

(54) SELF-GOVERNING MEDICAL PEER RATING SYSTEM FOR HEALTH MANAGEMENT CONTENT

(75) Inventor: Rocky Shaw, Mountain View, CA (US)

(73) Assignee: Robert Bosch Healthcare Systems, Inc., Palo Alto, CA (US)

( * ) Notice: Subject to any disclaimer, the term of this patent is extended or adjusted under 35 U.S.C. 154(b) by 325 days.

(21) Appl. No.: 12/896,437

(22) Filed: Oct. 1, 2010

(65) Prior Publication Data

US 2012/0084434 A1 Apr. 5, 2012

(51) Int. Cl.
*G06F 15/173* (2006.01)

(52) U.S. Cl.
USPC .......................................................... 709/224

(58) Field of Classification Search
USPC .......................................................... 709/224
See application file for complete search history.

(56) References Cited

U.S. PATENT DOCUMENTS

| | | | |
|---|---|---|---|
| 6,347,332 B1 | 2/2002 | Malet et al. | |
| 6,389,372 B1 | 5/2002 | Glance et al. | |
| 7,007,232 B1 * | 2/2006 | Ross et al. | 715/208 |
| 8,150,842 B2 * | 4/2012 | Brougher et al. | 707/723 |
| 2002/0198866 A1 | 12/2002 | Kraft et al. | |
| 2005/0203866 A1 | 9/2005 | Daud et al. | |
| 2005/0256796 A1 | 11/2005 | Haga et al. | |
| 2006/0282336 A1 | 12/2006 | Huang | |
| 2009/0204426 A1 * | 8/2009 | Thorne et al. | 705/2 |

* cited by examiner

*Primary Examiner* — Ryan Jakovac
(74) *Attorney, Agent, or Firm* — Rahman LLC

(57) ABSTRACT

A self-governing medical peer rating system for evaluating and rating health management content includes a subject matter expert (SME) registration module that accepts a subscription from an SME to an application for contribution of content by entering credentials of the SME into the medical peer rating system, a SME verification module that verifies a profile of the SME created by the SME, a SME approval module that approves the SME as a verified SME based on at least one of a positive feedback, a negative feedback, and a neutral feedback from a group of verified SMEs, a community member, and a member of an editorial board. A content creator module that creates the content contributed by the SME. A content approval module that approves the content upon the content being discussed or reviewed by any of the verified SMEs, the community member, and the member of the editorial board.

13 Claims, 10 Drawing Sheets

| SMEs 502 | APPROVE 504 | REJECT 506 | DISCUSS 508 | TOTAL TO GIVE 510 |
|---|---|---|---|---|
| SME1 587 | +45 | -5 | DISCUSS | 50 |
| SME2 456 | +27 | -23 | DISCUSS | 50 |
| SME3 322 | +35 | 0 | DISCUSS | 35 |
| SME4 321 | +25 | -10 | DISCUSS | 35 |
| SME5 287 | +25 | -5 | DISCUSS | 30 |
| | +157 | (-43) | | 200 |
| NEW SME 0 | APPROVED | | | +157 |

FIG. 5

SELF-GOVERNING MEDICAL PEER RATING SYSTEM FOR HEALTH MANAGEMENT CONTENT

BACKGROUND

1. Technical Field

The embodiments herein generally relate to a content evaluation and rating system, and, more specifically to a self-governing medical peer rating system for health management content.

2. Description of the Related Art

Content on various subjects is available online through websites such as content and document management systems for publishing content from journals, review and rating websites, blogs, online encyclopedias, etc. Feedback and rating websites enable users to review and rate articles, movies and restaurants etc. to facilitate other users to make informed decisions based on the ratings. Blogs provide a platform for anyone to contribute fictional or non-fictional stories and educational material on disparate subjects. They also provide options for readers to comment and review content in an interactive manner. Electronic encyclopedias enable end-users to contribute content on a wide range of topics. This contributed content may be read, reviewed, edited, corrected, and improved by others.

The content management systems and document management systems allow users to create, review, edit, and approve content for the purpose of publishing electronic data. For example, a medical peer review citation index for publications involves independent reviews from a network of selected physicians by a company offering the peer review service. E-commerce or auction websites use rating systems for individual buyers, sellers, suppliers etc. based on parameters such as quality, price, opinions etc. There are community rating systems for contributors and content. However in these rating systems, every reviewer is treated equally. In specialized topics such as healthcare, although a multitude of users may have opinions, only a practitioner's opinion can be relied upon to make health related decisions.

In these existing online platforms for ratings and review, ratings are assigned to content based on opinions and experience, but not based on reliability. Generally, there is no process for verifying if the content is from a credible source. Further, not all transactions, written content and users are rated. Ratings that are within a community are restrictive. Points are given to those users who provide more content, regardless of its quality or accuracy. In addition, published journals become outdated quickly and there is a need to upgrade the medical journals from time to time. Accordingly there is a need for a specialized self-governing peer rating system, particularly for content related to health management.

SUMMARY

In view of the foregoing, an embodiment herein provides a self-governing medical peer rating system for evaluating and rating health management content. The self-governing medical peer rating system includes a subject matter expert (SME) registration module that accepts a subscription from an SME to an application for contribution of content. The SME subscribes to the self-governing medical peer rating system by entering credentials of the SME into the medical peer rating system. The credentials include at least one of a certification, school, licensure, and status associated with the SME. A SME verification module that verifies a profile of the SME created by the SME. The profile includes at least one of a name, a location, a hospitals/clinics worked, experience of practicing, restrictions, awards, journals/articles published, and a topic of interest associated with the SME.

A SME approval module approves the SME as a verified SME based on at least one of a positive feedback, a negative feedback, and a neutral feedback from any of a group of verified SMEs, a community member, and at least one member of an editorial board. A content creator module creates the content contributed by the SME. The SME contributes the health management content on the SME being verified. The content creator module includes a content notification module that transmits a notification to the group of verified SMEs, the community member, and the member of an editorial board, upon the content being contributed by the SME. The notification includes at least one of the content for discussion, reviewing, and approval. A content approval module approves the content upon the content being discussed or reviewed by any of the verified SMEs, the community member, and the member of the editorial board. New content is placed in a pending state of acceptance until the new content is approved by any of the verified SMEs, the community member, and the member of the editorial board.

A content management module manages the content being contributed by the verified SMEs. A content publishing module publishes the content being approved by the verified SMEs, the community member, and the member of the editorial board in a content library. The content includes any of the health management content and a wellness program. An account is set by end users to automatically update the content and the wellness program upon being approved and published by any of the verified SMEs, the community member, and the member of the editorial board. Any of the group of verified SMEs, the community member, and the member of the editorial board are notified based on any of a point level and a ranking associated with the group of verified SMEs, the community member, and the member of the editorial board upon the content being contributed by the verified SME when the content is of a category associated with any of the group of verified SMEs, the community member, and the member of the editorial board.

The content is published and accepted in the content library by the community member based on any of a feedback and a qualifying percentage of acceptances. A status of the content is changed from the pending state of acceptance to an accept state based on a positive level point system. Any of the content and the wellness program is delivered to end users using any of a telehealth appliance, an Internet service, an interactive television program, a handheld devices, and a telephonic script. The point level, and the ranking is based on any of a positive feedback and a negative feedback received from any of a member of the group of SMEs, the community member, and the member of the editorial board.

A database stores information associated with the group of verified SMEs, the community member, and the member of the editorial board. An updating module updates the content with the new content. The verified SMEs update the content on a case-by-case basis. The verified SME receives a points level from the group of verified SMEs. The points level received is determined based on a rank and a ranking associated with the group of verified SMEs.

In another aspect, a medical peer rating system for health management content is provided. The medical peer rating system includes a subject matter expert (SME) registration and verification module that receives credentials of a SME willing to edit content of medical-related literature and to verify credentials of a creator of the literature. The credentials include at least one of a certification, school, licensure, and status associated with the SME. A content editor module receives input content related to health management from a verified SME that is verified by a SME verification module based on professional credentials and a profile of the verified SME. A content approver module circulates the received input content among other SMEs for assessment, rating, and approval. A content management module notifies subscribers of data content regarding availability of updated content when input data content is approved by other SMEs. A content publishing updates the data content in a content library based on the approval of the input data content.

The SME registration and verification module receives an input profile of the SME willing to modify or update the content of medical-related literature. The input profile includes a name, location, hospitals or clinics worked, experience, restrictions, awards received, journals or articles published, and field of specialization of the SME. The content editor module receives content for modification or updating from an approved SME. The received input content is circulated among designated SMEs based on preset rules for review and rating. The content management module sends notification to all subscribers of available updated content, when the input data content is approved. The content publishing module updates the data content in the content library with the approved input data content and publishes the approved data content.

In yet another aspect, a method of rating and evaluating content contributed by an SME in a self-governing medical peer rating system is provided. The self-governing medical peer rating system includes a medical peer rating server. The SME subscribes to an application for contribution of the content by entering at least one of a certifications, schools, licensure, and status. The method includes verifying a profile of the SME that includes at least one of a name, a location, a hospitals/clinics worked, experience of practicing, restrictions, awards, journals/articles published, and a topic of interest associated with the SME, processing the SME as a verified SME based on any of a positive feedback, a negative feedback, and a neutral feedback from a group of verified SMEs, at least one of a community member, and at least one member of an editorial board based on the profile being verified, receiving the content from the verified SME for contribution, communicating a notification to the group of verified SMEs, the community member, and the member of an editorial board, on the new content being received by the SME, when the new content is of a category associated with any of the group of verified SMEs, the community member, and the member of the editorial board, processing a status of the content from a pending state of acceptance to an accept state based on a points level, publishing the content being discussed, reviewed, or accepted by any of the verified SMEs, the community member, and the member in a content library based on the points level, communicating the content to end users using any of a telehealth appliance, an Internet service, an interactive television program, a handheld device, and a telephonic script, and updating the content with new content upon being contributed by the SME.

The content includes any of the health management content and a wellness program. The group of verified SMEs, the community member, and the member of an editorial board are notified based on any of a point level and a ranking associated with the group of verified SMEs, the community member, and the member of an editorial board. The status of the content is changed to the accept state upon the content being discussed or reviewed by any of the group of verified SMEs, the community member, and the member of the editorial board. The content is published and accepted in the content library by the community member based on any of a feedback and a qualifying percentage of acceptances. The point level and the ranking is based on any of a positive feedback and a negative feedback received from any of a member of the group of SMEs, the community member, and the member of the editorial board.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 5 illustrates a table view of the SME approval module of FIG. 2 of the medical peer rating server of FIG. 1 according to an embodiment herein;

DETAILED DESCRIPTION OF PREFERRED EMBODIMENTS

Figure 1:
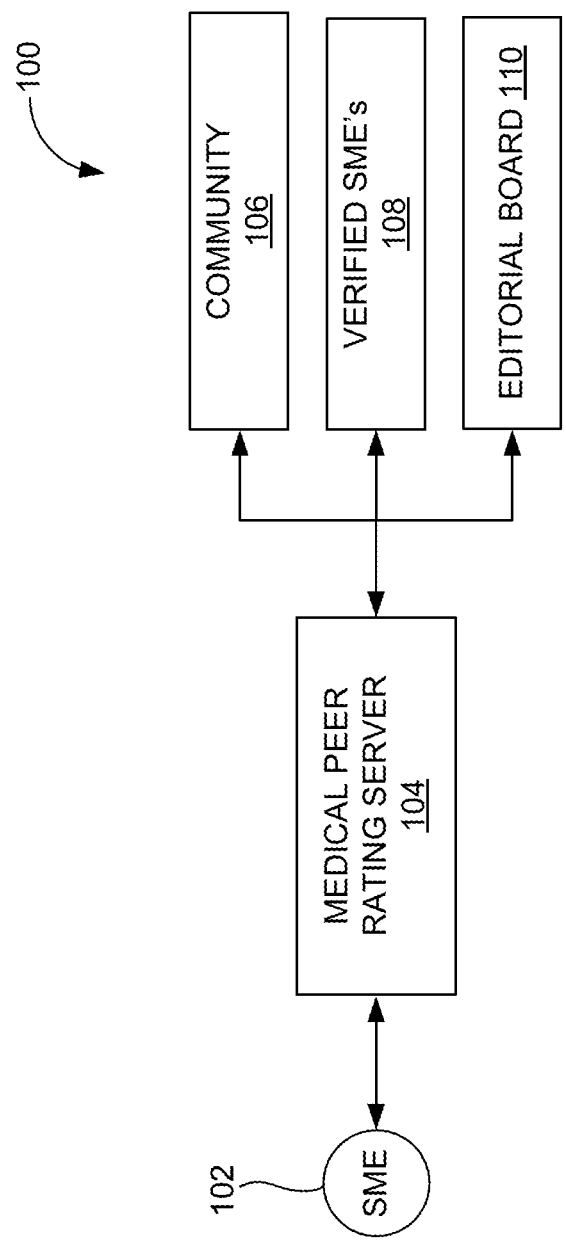
FIG. 1 is a system view of a self-governing medical peer rating system illustrating a subject matter expert (SME) communicating with a community, a group of verified SMEs, and members of an editorial board for registering to a medical peer rating server to contribute a health management content according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there is a need for a specialized self-governing peer rating system, particularly for content related to health management. The embodiments herein achieve this by providing a medical peer rating system to authorize the SME to subscribe the contents related to the health management system. Referring now to the drawings, and more particularly to FIG. 1 through FIG. 10, where similar reference characters denote corresponding features consistently throughout the figures, there are shown preferred embodiments.

FIG. 1 is a system view of a self-governing medical peer rating system 100 illustrating an SME 102 communicating with a community 106, a group of verified SMEs 108, and members of an editorial board 110 for registering to a medical peer rating server 104 to contribute health management content according to an embodiment herein. The SME 102 subscribes to an application for contribution of the health management content by entering at least one of a certifications, schools, licensure, and status, etc. In one embodiment, the SME 102 may be any of a clinician, such as MD, nurse, pharmacist, nutritionist, PHD, clinical expert, or health institution, and may be configured as a database of information stored in a computer or other communication device. The certifications may be educational details in any of a country/place (e.g., USA, Europe, Asia, etc.). The community 106, the group of verified SMEs 108, and the members of the editorial board 110 verify a profile of the SME 102 based on a name, a location, hospitals/clinics worked, experience of practicing, restrictions, awards, journals/articles published, and a topic of interest associated with the SME 102.

The community 106, the group of verified SMEs 108, and the members of the editorial board 110 discuss, and/or review the profile and approve the SME 102 as one of the verified SME based on a positive feedback, a negative feedback, and/or a neutral feedback from the group of verified SMEs 108, the community 106, and the member of an editorial board 110. In one embodiment, the SME 102 can only contribute health management content once he/she is approved and verified by the group of verified SMEs 108, the community 106, and the member of an editorial board 110.

Figure 2:
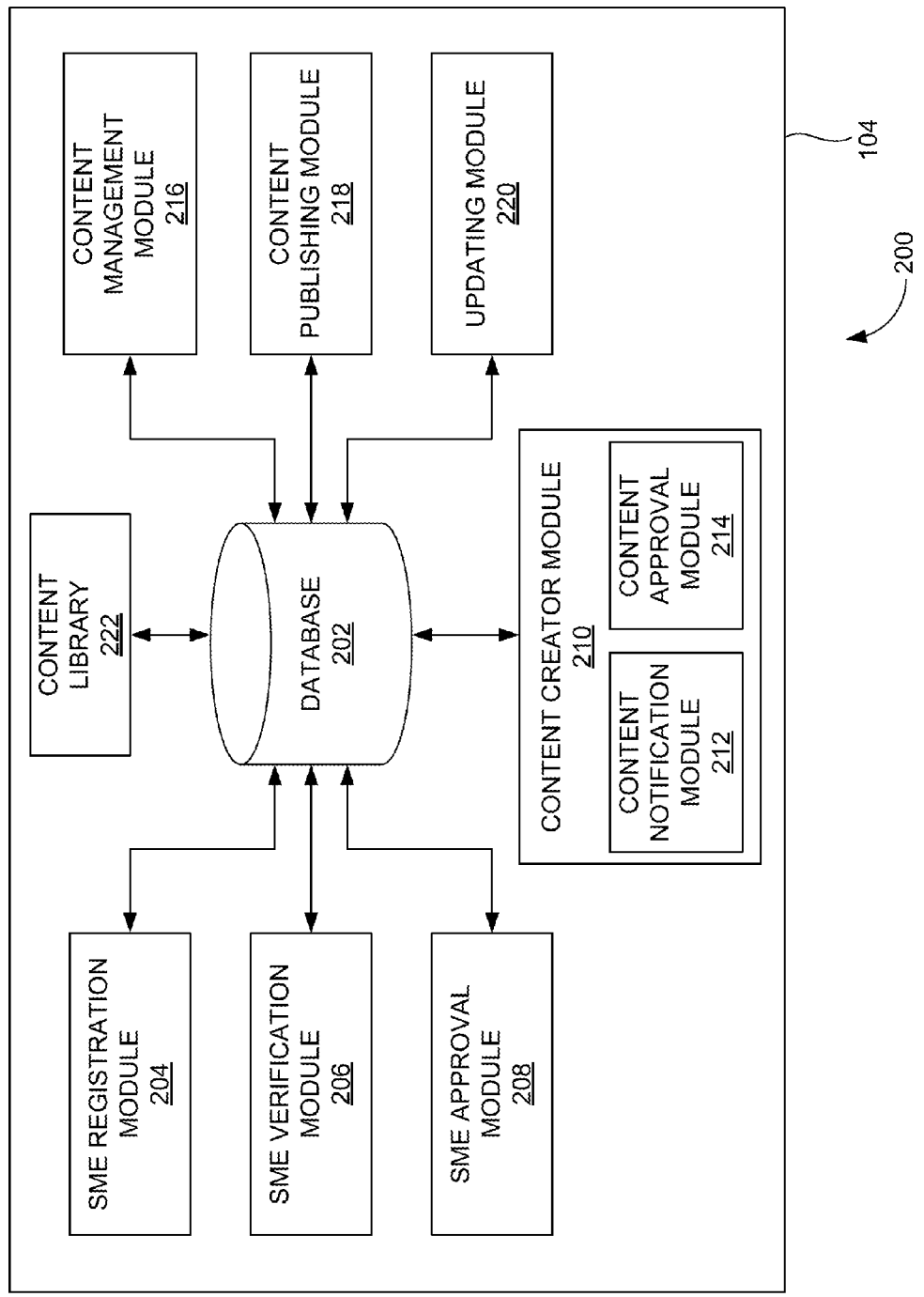
FIG. 2 illustrates an exploded view of the medical peer rating server of FIG. 1 according to an embodiment herein.

FIG. 2, with reference to FIG. 1, illustrates an exploded view 200 of the medical peer rating server 104 of FIG. 1 according to an embodiment herein. The medical peer rating server 104 includes a database 202, a SME registration module 204, a SME verification module 206, a SME approval module 208, a content creator module 210, a content notification module 212, a content approval module 214, a content management module 216, a content publishing module 218, an updating module 220, and a content library 222. The database 202 stores information associated with the SME 102, the community 106, a group of verified SMEs 108, and the members of the editorial board 110. The database 202 further includes health management content contributed by various SMEs, and the community 106, the group of verified SMEs 108, the members of the editorial board 110.

The SME registration module 204 registers and/or accepts a subscription from the SME 102 for contribution of content. The SME registration module 204 receives an input profile of the SME who is willing to modify or update the content of medical-related literature. The SME 102 subscribes to the self-governing medical peer rating system 100 by entering credentials such as certifications, schools, licensure, and/or status, etc. The SME verification module 206 verifies a profile of the SME 102 created by the SME 102. The profile may include details of the SME 102 such as name, location, hospitals/clinics worked, experience of practicing, restrictions, awards, journals/articles published, and a topic of interest/field of specialization associated with the SME 102.

The SME approval module 208 approves the SME 102 as a verified SME based on any of a positive feedback, a negative feedback, and/or a neutral feedback received from the community 106, the group of verified SMEs 108, and members of the editorial board 110. In one embodiment, the medical peer rating server 104 of FIG. 1 may include a content editor module (not shown in FIG. 2) that receives content for modification or updating from an approved/verified SME. The received input content is circulated among designated SMEs based on preset rules for review and rating. The verified SMEs 108 update the content on a case-by-case basis. The verified SME 108 receives a points level from the group of verified SMEs 108.

The points level received is determined based on a rank and a ranking associated with the group of verified SMEs 108. The content creator module 210 creates the content contributed by the SME 102. In one embodiment, the content creator module 210 creates the content only if the SME 102 is a verified SME. The content notification module 212 transmits a notification to the group of verified SMEs 108, the community 106, and/or the member of the editorial board 110 on receiving the content contributed by the SME 102. The content is further reviewed and/or discussed within the group of verified SMEs 108, the community 106, and/or the member of the editorial board 110 for approval.

In one embodiment, the community 106, the group of verified SMEs 108, and/or the member of the editorial board 110 are notified based on a point level, or a ranking associated with the group of verified SMEs 108, the member of the editorial board 110, and the community 110. In another embodiment, the notification is sent to the community 106, the group of verified SMEs 108, and/or the member of the editorial board 110 if the content is of a category associated with the group of verified SMEs 108, the community 106, and/or the member of the editorial board 110. For example, if the content contributed to diabetes disease, then only the group of verified SMEs 108, the community 106, and/or the member of the editorial board 110 are notified who are in this category. In another embodiment, the point level, and the ranking is based on a positive feedback, or a negative feedback received from any of a member of the group of SMEs, the community, or the member of the editorial board.

The content approval module 214 approves the content after being discussed, or reviewed by any of the verified SMEs 108, the community 106, or the members of the editorial board 110. In one embodiment, the content is in a pending state until the content is approved by any of the community 106, the group of the verified SMEs 108, or the member of the editorial board 110. The content management module 216 manages the content contributed by the verified SME (e.g., the SME 102 of FIG. 1). In one embodiment, the content management module 216 sends notification to all subscribers of available updated content, when the input data content is approved. The content publishing module 218 publishes the content upon being verified and approved by the community 106, the group of verified SMEs 108, and/or the members of the editorial board 110 in the content library 222. In one embodiment, the content is published and accepted in the content library 222 based on feedback, and/or a qualifying percentage of acceptances. In another embodiment, the content publishing module 218 updates the data content in the content library 222 with the approved input data content and publishes the approved data content. The updating module 220 updates the content with a new content when the SME 102 adds content to the existing content.

Figure 3:
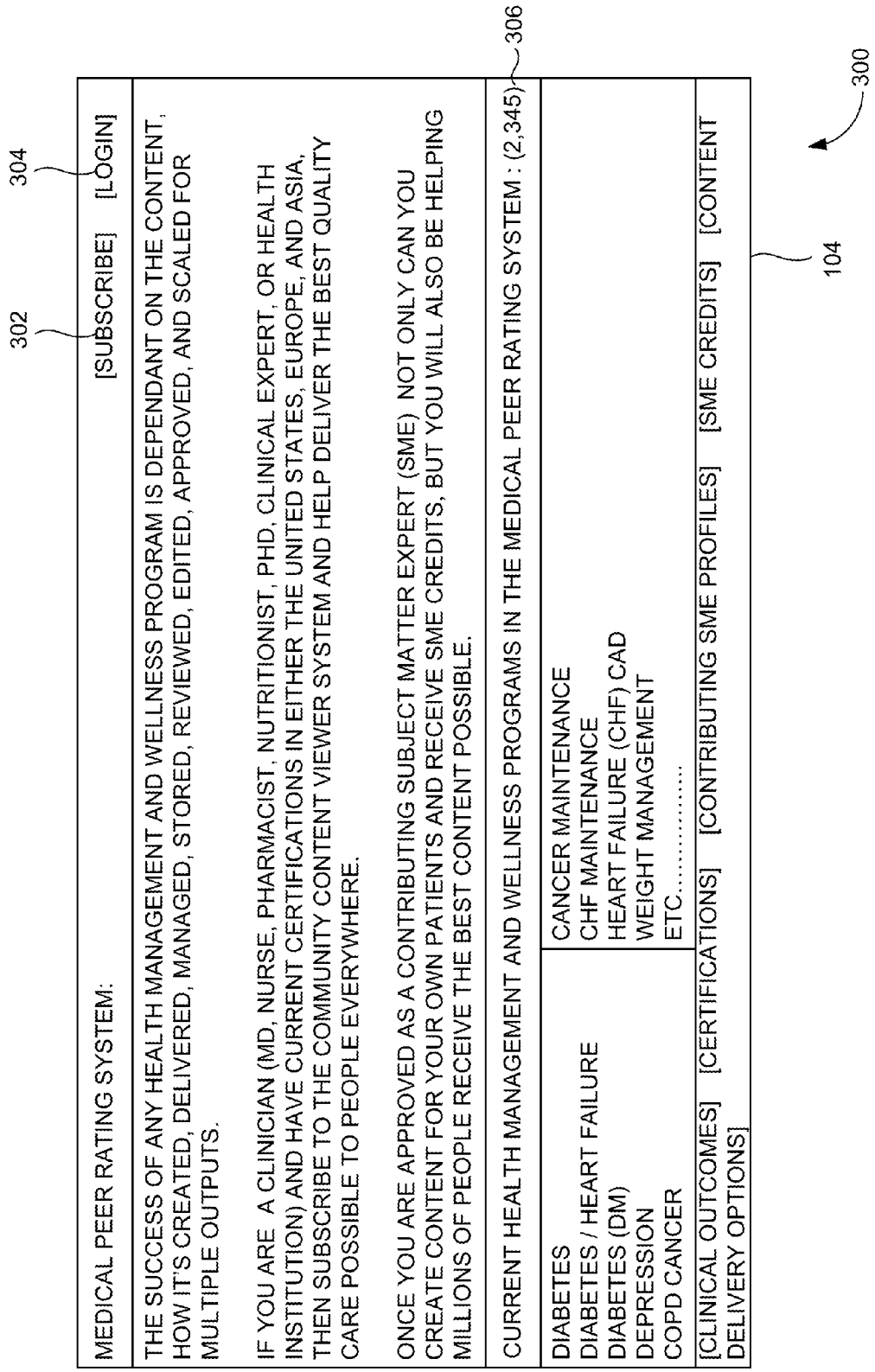
FIG. 3 illustrates a user interface view of the medical peer rating server of FIG. 1 according to an embodiment herein.

FIG. 3, with reference to FIGS. 1 and 2, illustrates a user interface 300 of the medical peer rating server 104 of FIG. 1 according to an embodiment herein. The user interface 300 of the medical peer rating server 104 includes a subscriber field 302, a login field 304, and a health management content and wellness programs field 306. The subscribe field 302 allows an SME (e.g., the SME 102) to subscribe to the medical peer rating server 104 for contributing health management content and wellness programs content. The login field 304 allows the SME 102 to login after being subscribed and verified as a verified SME by the community 106, the group of the verified SMEs 108, or the member of the editorial board 110.

In one embodiment, end users may also subscribe and/or login to the medical peer rating server 104. In another embodiment, end users may also contribute content associated with the health management and wellness programs. In yet another embodiment, the end users may set an account to automatically update the content and the wellness programs upon being approved and published by the verified SMEs 108, the community 106, or the member of the editorial board 110. The content, or the wellness programs is delivered to end users via any of a telehealth appliance, an Internet service, an interactive television program, handheld communication devices, or a telephonic script. The health management content and wellness programs field 306 displays a list of health management content and wellness programs in the medical peer rating server 104. The list of health management content and wellness programs may include content related to, for example, diabetes, heart failure, diabetes (DM), depression, COPD cancer, cancer maintenance, CHF maintenance, heart failure (CHF) CAD, weight management, etc. Additionally, the SME 102, the community 106, the group of the verified SMEs 108, or the members of the editorial board 110 may view clinical outcomes, certifications, contributing SME profiles, SME credits details, and content delivery in the medical peer rating server 104.

Figure 4:
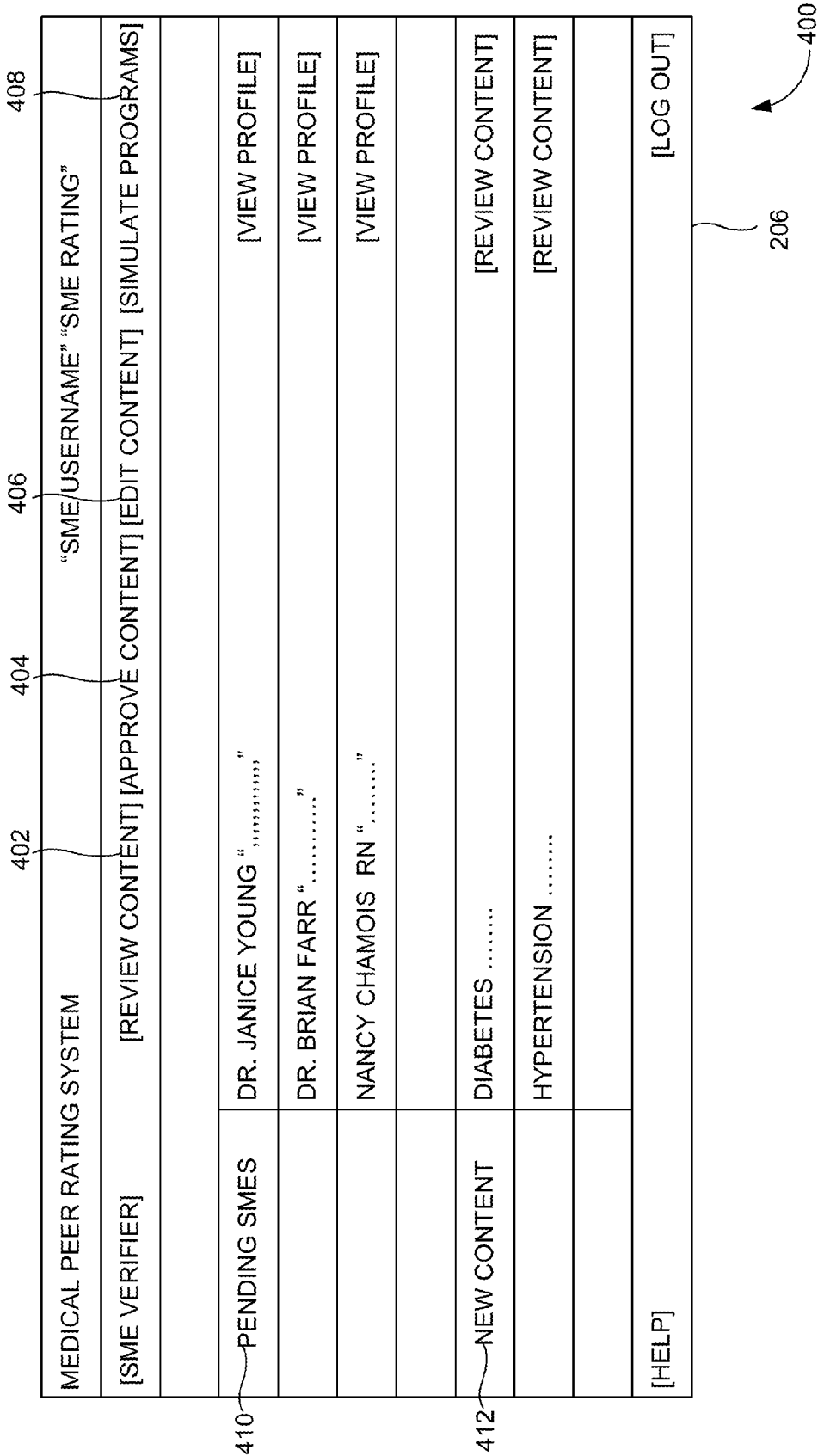
FIG. 4 illustrates a user interface view of the SME verification module of FIG. 2 of the medical peer rating server of FIG. 1 according to an embodiment herein.

FIG. 4, with reference to FIGS. 1 through 3, illustrates a user interface 400 of the SME verification module 206 of FIG. 2 of the medical peer rating server 104 of FIG. 1 according to an embodiment herein. The user interface 400 of the SME verification module 206 includes a review content field 402, an approve content field 404, an edit content field 406, a simulate program field 408, a pending SMEs field 410, and a new content field 412. The review content field 402 allows the community 106, the group of the verified SMEs 108, or the member of the editorial board 110 to review the content contributed by the SME 102. The approve content field 404 approves the content of the SME 102 when the community 106, the group of the verified SMEs 108, or the member of the editorial board 110 selects the field to approve the content based on a discussion and/or review.

The edit content field 406 allows the community 106, the group of the verified SMEs 108, or the member of the editorial board 110 to edit the content contributed by the SME 102. The simulate programs field 408 allows the community 106, the group of the verified SMEs 108, or the member of the editorial board 110 to simulate the content based on the approval. The pending SMEs field 410 includes a list of the SMEs (e.g., the SME 102 of FIG. 1) to be approved and verified. The community 106, the group of the verified SMEs 108, or the member of the editorial board 110 may view the SMEs profile (e.g., Dr. Janice Young profile, Dr. Brain Farr profile, or Nancy Chamois RN profile) by clicking on the view profile option. The new content field 412 includes a content associated with the health management and/or wellness programs (e.g., diabetes, and/or hypertension) that is contributed by the SME 102 for review. The community 106, the group of the verified SMEs 108, or the member of the editorial board 110 may review the content contributed by the SMEs (e.g., Dr. Janice Young, Dr. Brain Farr, or Nancy Chamois RN).

FIG. 5, with reference to FIGS. 1 through 4, illustrates a table 500 of the SME approval module 208 of FIG. 2 of the medical peer rating server 104 of FIG. 1 according to an embodiment herein. The table 500 of the SME approval module 208 includes a SMEs field 502, an approve field 504, a reject field 506, a discuss field 508, and a total to give field 510. The SMEs field 502 includes a list of SMEs (e.g., SME1 587, SME2 456, SME3 322, SME4 321, and SME5 287) for approval. The approve field 504 includes a point level for each of the SME (e.g., the SME 102 of FIG. 1) to be approved and accepted as a verified SME. The points for approve field 504 indicates a positive feedback. The reject field 506 includes a point level for each of the SME (e.g., the SME 102 of FIG. 1) to be rejected. In an example embodiment, for the SME 1 587 the point level for approve is +45, and −5 for reject. For the SME 2 456, the point level for approve is +27, and −23 for reject. For the SME3 322, the point level for approve is +35, and 0 for reject. For the SME4 321, the point level for approve is +25, and −10 for reject. For the SME5 287, the point level for approve is +25, and −5 for reject.

The discuss field 506 indicates the status for each of the SME 102. For example, the discuss field 506 indicates "DISCUSS" status for each of the SME (e.g., SME1 587, SME2 456, SME3 322, SME4 321, and SME5 287). The total to give field 508 includes the total point levels to be assigned to each of the SME. For example, the total points to give to SME1 587 is 50 points. The total points to give to SME2 456 is 50 points. The total points to give to SME3 322 is 35 points. The total points to give to SME4 321 is 35 points. The total points to give to SME5 287 is 30 points. The table 500 indicates the approval or the pending status of the SMEs.

Figure 6:
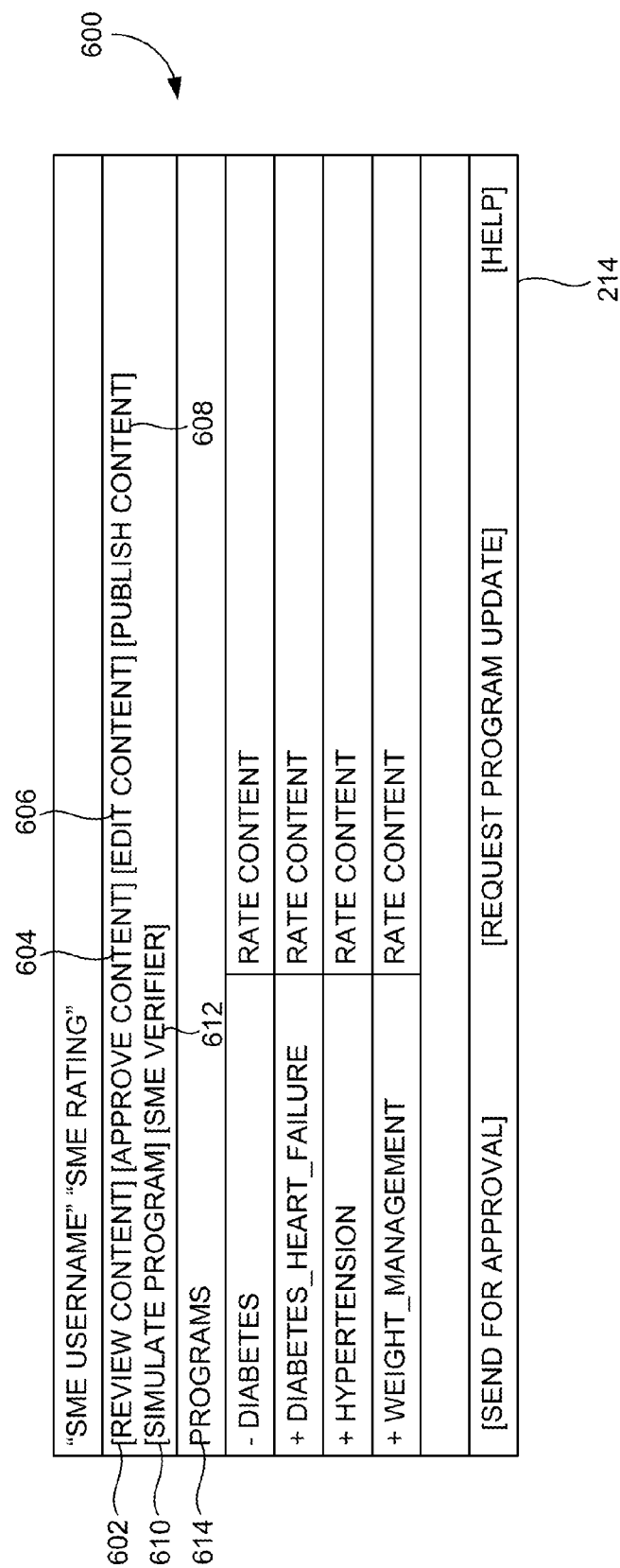
FIG. 6 illustrates a user interface view of the content approval module of FIG. 2 of the medical peer rating server of FIG. 1 according to an embodiment herein.

FIG. 6, with reference to FIGS. 1 through 5, illustrates a user interface 600 of the content approval module 214 of FIG. 2 of the medical peer rating server 104 of FIG. 1 according to an embodiment herein. The user interface 600 of the content approval module 214 includes a review content field 602, an approve content field 604, an edit content field 606, a publish content field 608, a simulate program field 610, a SME verifier field 612, and a programs field 614. The review content field 602 allows the community 106, the group of the verified SMEs 108, or the member of the editorial board 110 to review the content contributed by the SME 102. The approve content field 604 approves the content of the SME 102 when the community 106, the group of the verified SMEs 108, or the member of the editorial board 110 selects the field to approve the content based on a discussion and/or review.

The edit content field 606 allows the community 106, the group of the verified SMEs 108, or the member of the editorial board 110 to edit the content contributed by the SME 102. The publish content field 608 allows the community 106, the group of the verified SMEs 108, or the member of the editorial board 110 to publish in content library 222 after the content is approved and accepted based on a feedback, or a qualifying percentage of acceptances. The simulate programs field 610 allows the community 106, the group of the verified SMEs 108, or the member of the editorial board 110 to simulate the content based on the approval. The SME verifier field 612 allows the community 106, the group of the verified SMEs 108, or the member of the editorial board 110 to verify the SME (e.g., the SME 102) based on the credentials and profile associated with the SME 102. The programs field 614 includes a list of wellness programs (e.g., diabetes, diabetes_ heart_failure, hypertension, and/or weight management. The community 106, the group of the verified SMEs 108, or the member of the editorial board 110 further may rate the content of the wellness programs.

Figure 7:
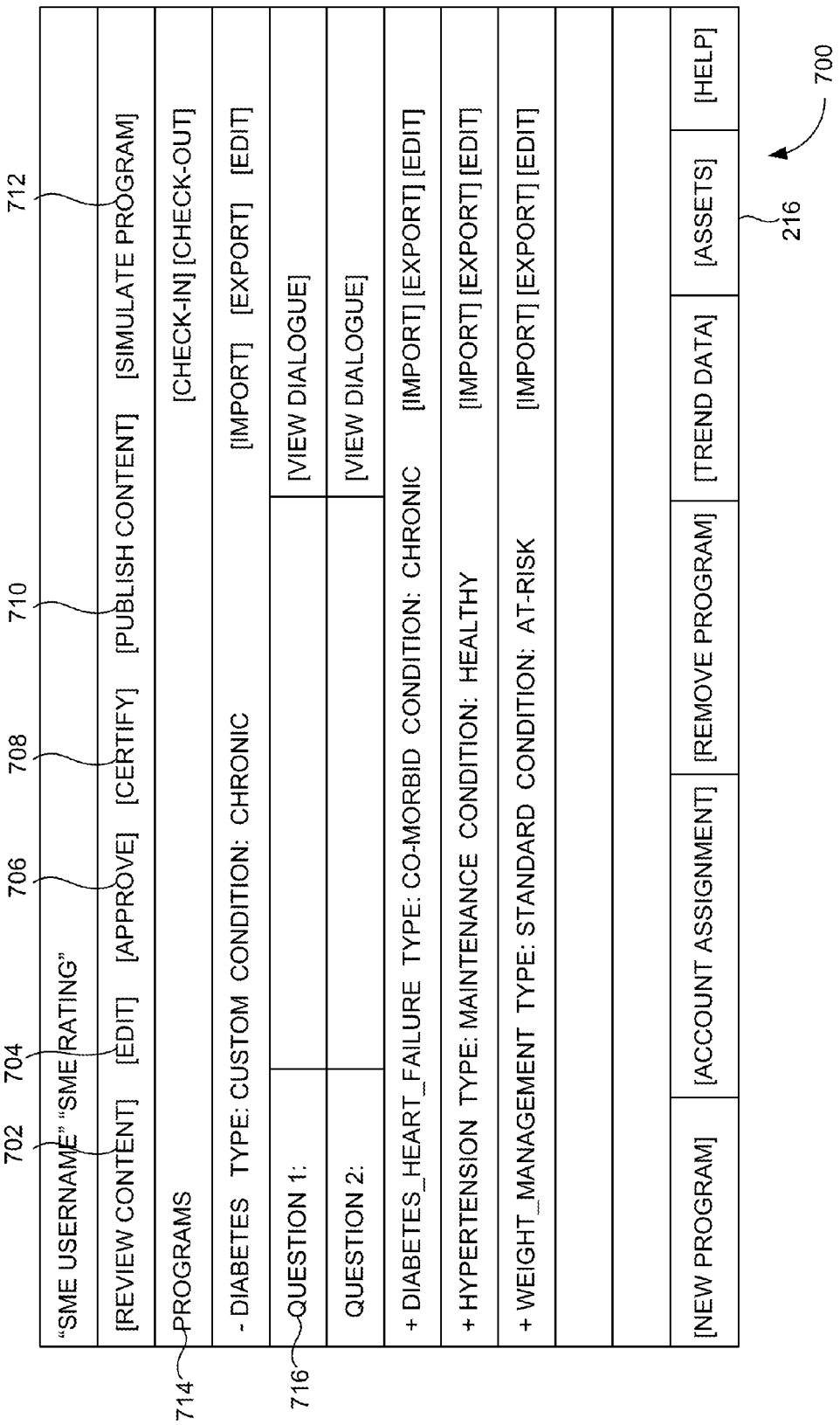
FIG. 7 illustrates a user interface view of the content management module of FIG. 2 of the medical peer rating server of FIG. 1 according to an embodiment herein.

FIG. 7, with reference to FIGS. 1 through 6, illustrates a user interface 700 of the content management module 216 of FIG. 2 of the medical peer rating server 104 of FIG. 1 according to an embodiment herein. The user interface 700 of the content management module 216 includes a review content field 702, an edit field 704, an approve field 706, a certify field 708, a publish content field 710, a simulate program field 712, a programs field 714, and a query field 716. The certify field 708 allows the community 106, the group of the verified SMEs 108, or the member of the editorial board 110 to check the certifications of the SME 102. The programs field 714 displays a list of programs (e.g., diabetes, diabetes_heart_failure, hypertension, and weight management) including a type, and a condition associated with the disease and the programs. The SME 102 may import, export, and/or edit the content of the programs by clicking the import, export and/or edit fields.

The query field 716 allows the SME 102 and/or users to submit a query related to the programs. Additionally, the community 106, the group of the verified SMEs 108, or the member of the editorial board 110 may view the details of the programs and the queries from the view dialogue field 718. Further, the SMEs (e.g., the SME 102 of FIG. 1) may view/add a new program, account assignments, remove program, assets, and ask for help.

Figure 8:
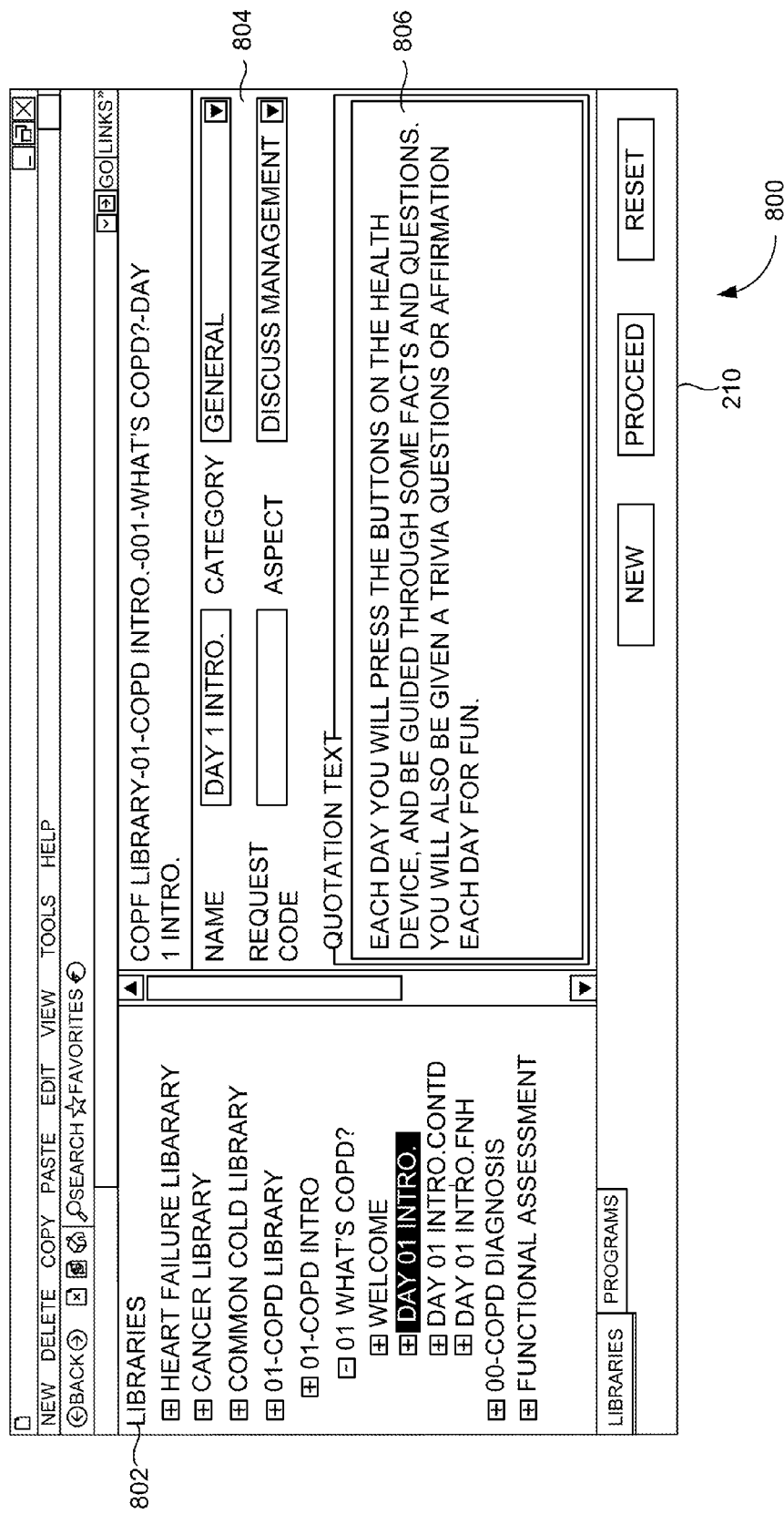
FIG. 8 illustrates a user interface view of the content creator module of FIG. 2 of the medical peer rating server of FIG. 1 according to an embodiment herein.

FIG. 8, with reference to FIGS. 1 through 7, illustrates a user interface 800 of the content creator module 210 of FIG. 2 of the medical peer rating server 104 of FIG. 1 according to an embodiment herein. The user interface 800 of the content creator module 210 includes a library field 802, an information field 804, and a quotation text field 806. The library field 802 includes a list of health management content and/or wellness programs. The SME 102 may navigate to a particular health management content or wellness program (e.g., What's COPD, day 01 intro, etc.). The information field 804 displays the information associated with the health management content or wellness program (e.g., What's COPD, day 01 intro, etc.). The quotation text field 806 includes a portion for the SME 102 to contribute health management content or details of the wellness program associated with the What's COPD, day 01 intro, etc. The SME 102 may add content (e.g., each day you will press the buttons on the health device, and be guided through some facts and questions. You will also be given a trivia question or affirmation each day for fun) to the respective health management content or wellness program in the content library 222.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly.

The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can include hardware and software embodiments. The embodiments that are implemented in software include but are not limited to, firmware, resident software, microcode, etc.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 9:
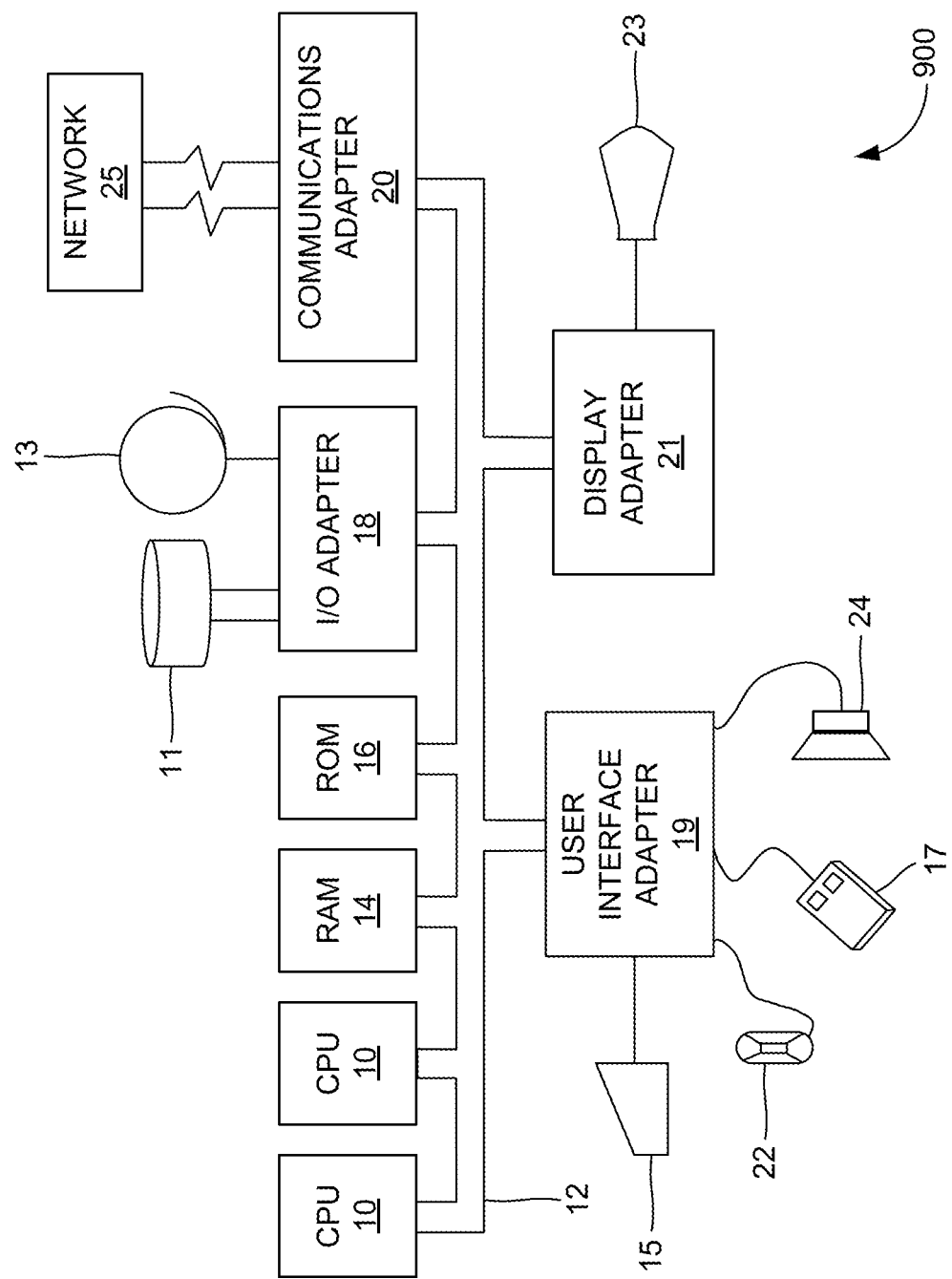
FIG. 9 illustrates a schematic diagram of a computer architecture used in accordance with the embodiment herein.

A representative hardware environment for practicing the embodiments herein is depicted in FIG. 9. This schematic drawing illustrates a hardware configuration of an information handling/computer system 900 in accordance with the embodiments herein. The system 900 comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system 900. The system 900 can read the inventive instructions on the program storage devices and follow these instructions to execute the methodology of the embodiments herein.

The system 900 further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

Figure 10:
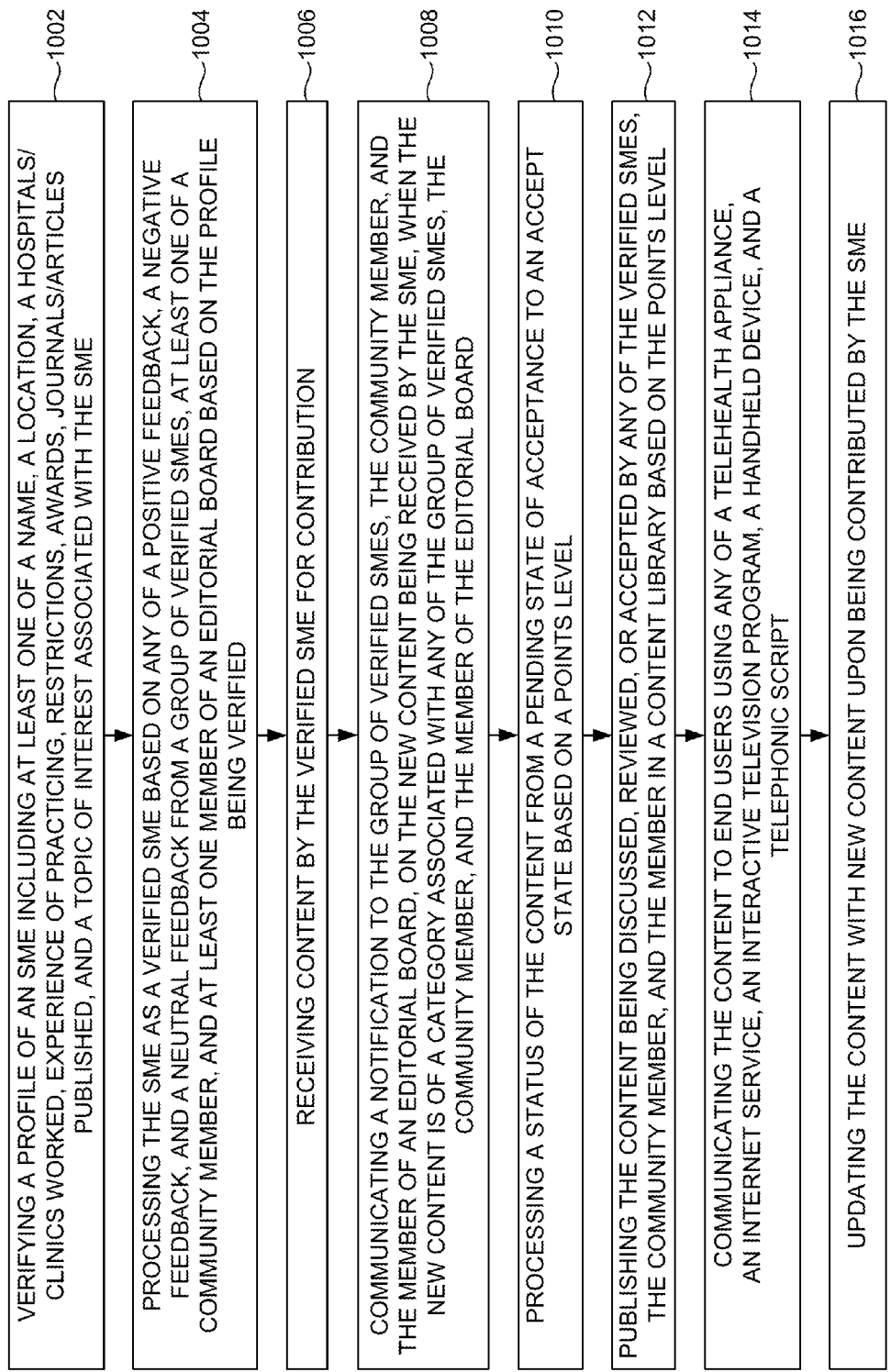
FIG. 10 is a flow diagram illustrating a method of rating and evaluating a content contributed by an SME in a self-governing medical peer rating system according to an embodiment herein.

FIG. 10, with reference to FIGS. 1 through 9, is a flow diagram illustrating a method of rating and evaluating content contributed by an SME 102 in a self-governing medical peer rating system 100 according to an embodiment herein. The self-governing medical peer rating system 100 includes a medical peer rating server 104. The SME 102 subscribes to an application for contribution of the content by entering at least one of a certifications, schools, licensure, and status (using the SME registration module 204). In one embodiment, in step 1002, a profile of the SME 102 including at least one of a name, a location, a hospitals/clinics worked, experience of practicing, restrictions, awards, journals/articles published, and a topic of interest associated with the SME 102 is verified (e.g., using the verification module 206). In step 1004, the SME 102 is processed as a verified SME based on any of a positive feedback, a negative feedback, and a neutral feedback from a group of verified SMEs 108, at least one of a community member 106, and at least one member of an editorial board 110 based on the profile being verified. In one embodiment, the SME approval module 208 processes the SME 102 as a verified SME.

In step 1006, content is received from the verified SME for contribution. In step 1008, a notification is communicated (e.g., using the content notification module 212) to the group of verified SMEs 108, the community member 106, and the member of an editorial board 110, on the new content being received by the SME 102, when the new content is of a category associated with any of the group of verified SMEs 108, the community member 106, and the member of the editorial board 110. The group of verified SMEs 108, the community member 106, and the member of an editorial board 110 are notified based on any of a point level and a ranking associated with the group of verified SMEs 108, the community member 106, and the member of the editorial board 110. The point level and the ranking is based on any of a positive feedback and a negative feedback received from any of a member of the group of SMEs 108, the community member 106, and the member of the editorial board 110.

In step 1010, a status of the content is processed from a pending state of acceptance to an accept state based on a points level (e.g., using the content approval module). The status of the content is changed to the accept state upon the content being discussed or reviewed by any of the group of verified SMEs 108, the community member 106, and the member of the editorial board 110. In step 1012, the content being discussed, reviewed, or accepted by any of the verified SMEs 108, the community member 106, and the member of the editorial board 110 in the content library 222 based on the points level is published. In one embodiment, the content publishing module 218 publishes the content.

In step 1014, the content is communicated to end users using any of a telehealth appliance, an Internet service, an interactive television program, a handheld device, and a telephonic script. The content is any of the health management content and a wellness program. In step 1016, the content is updated with new content upon being contributed by the SME 102. In one embodiment, the updating module 220 updates the content with the new content. The content is published and accepted in the content library 222 by the community member 106 based on any of a feedback and a qualifying percentage of acceptances.

The self-governing medical peer rating system 100 provides the community 106, verified SMEs 108, and the members of the editorial board 110 to review, approve, and rank medical content such as health management content and wellness programs. The system 100 provides a medical content peer rating system to generate a pool of qualified subject matter specialists/experts 102 for each category to contribute health management content and to evaluate the newly created content. The system 100 provides a manner of judging whether the newly created and written content should be accepted approved as a part of a recommended content library 222. The system 100 is used to distribute the health management content into treatment programs for end users. The newly generated content may be verified by the medical peer rating server 104 in a controlled environment. The health management and wellness programs may be delivered to end users through specialized health appliances, the Internet, interactive television, handheld devices, and telephonic scripts. The system 100 is used to generate content that is stored in a standard markup language and that may be understood by disparate applications. The system further allows the submission of automated content certification (NCQA).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A self-governing medical peer rating system for evaluating and rating health management content, said self-governing medical peer rating system comprising:
   a server operatively coupled to a processor and comprising:
   a subject matter expert (SME) registration module that accepts a subscription from an SME to an application for contribution of said health management content, wherein said SME subscribes to said self-governing medical peer rating system by entering credentials of said SME into said medical peer rating system, wherein said credentials comprises at least one of a certification, school, licensure, and status associated with said SME;
   a SME verification module that verifies a profile of said SME created by said SME, wherein said profile comprises at least one of a name, a location, a hospitals/clinics worked, experience of practicing, restrictions, awards, journals/articles published, and a topic of interest associated with said SME;
   a SME approval module that approves said SME as a verified SME based on at least one of a positive feedback, a negative feedback, and a neutral feedback from any of a group of verified SMEs, a healthcare community member, and at least one member of an editorial board;

a content creator module that creates said health management content contributed by said SME, wherein said SME contributes said health management content on said SME being verified, said content creator module comprising:

a content notification module that transmits a notification to said group of verified SMEs, said healthcare community member, and said member of an editorial board, upon said health management content being contributed by said SME, wherein said notification comprises at least one of said health management content for discussion, reviewing, and approval; and a content approval module that approves said health management content upon said health management content being discussed or reviewed by any of said verified SMEs, said healthcare community member, and said member of said editorial board, wherein said health management content is placed in a pending state of acceptance until said health management content is approved by any of said verified SMEs, said healthcare community member, and said member of said editorial board;

a content management module that manages said health management content being contributed by said verified SMEs; and a content publishing module that publishes said health management content for viewing by end users, upon said health management content being approved by said verified SMEs, said healthcare community member, and said member of said editorial board in a content library, wherein said health management content comprises a wellness program.

2. The self-governing medical peer rating system of claim 1, further comprising an account set by end users to automatically update said health management content upon being approved and published by any of said verified SMEs, said healthcare community member, and said member of said editorial board.

3. The self-governing medical peer rating system of claim 1, wherein any of said group of verified SMEs, said healthcare community member, and said member of said editorial board are notified when said health management content is of a category associated with any of said group of verified SMEs, said healthcare community member, and said member of said editorial board.

4. The self-governing medical peer rating system of claim 1, wherein said health management content is published and accepted in said content library by said healthcare community member based on any of a feedback and a qualifying percentage of acceptances.

5. The self-governing medical peer rating system of claim 1, wherein a status of said health management content is changed from said pending state of acceptance to an accept state based on a positive level point system.

6. The self-governing medical peer rating system of claim 2, wherein said health management content is delivered to end users using any of a telehealth appliance, an Internet service, an interactive television program, a handheld device, and a telephonic script.

7. The self-governing medical peer rating system of claim 3, wherein said group of SMEs, said community member, and said member of said editorial board are notified about said health management content based on a point level and a ranking, wherein said point level and said ranking is based on any of a positive feedback and a negative feedback received from any of a member of said group of SMEs, said community member, and said member of said editorial board.

8. The self-governing medical peer rating system of claim 1, further comprising a database that stores information associated with said group of verified SMEs, said community member, and said member of said editorial board.

9. The self-governing medical peer rating system of claim 8, further comprising an updating module that updates said health management content with new content.

10. The self-governing medical peer rating system of claim 1, wherein said verified SMEs update said health management content on a case-by-case basis, wherein said verified SME receives a points level from said group of verified SMEs, and wherein said points level received is determined based on a rank and a ranking associated with said group of verified SMEs.

11. A method of rating and evaluating health management content contributed by an SME in a self-governing medical peer rating system, said self-governing medical peer rating system comprising a medical peer rating server, wherein said SME subscribes to an application for contribution of said health management content by entering at least one of a certifications, schools, licensure, and status, said method comprising:

verifying a profile of said SME comprising at least one of a name, a location, a hospitals/clinics worked, experience of practicing, restrictions, awards, journals/articles published, and a topic of interest associated with said SME;

processing said SME as a verified SME based on any of a positive feedback, a negative feedback, and a neutral feedback from a group of verified SMEs, at least one of a healthcare community member, and at least one member of an editorial board based on said profile being verified;

receiving said health management content from said verified SME for contribution;

communicating a notification to said group of verified SMEs, said healthcare community member, and said member of an editorial board, on said health management content being received by said SME, when said health management content is of a category associated with any of said group of verified SMEs, said healthcare community member, and said member of said editorial board;

processing a status of said health management content from a pending state of acceptance to an accept state based on a points level, wherein said point level of said health management content is determined after discussion or review by any of said group of verified SMEs, said healthcare community member, and said member of said editorial board;

publishing said health management content being discussed, reviewed, or accepted by any of said verified SMEs, said healthcare community member, and said member in a content library based on said points level;

communicating said health management content to end users using any of a telehealth appliance, an Internet service, an interactive television program, a handheld device, and a telephonic script, wherein said health management content comprises a wellness program; and updating said health management content with new content upon being contributed by said SME.

12. The method of claim 11, wherein said health management content is published and accepted in said content library by said healthcare community member based on any of a feedback and a qualifying percentage of acceptances.

13. The method of claim 11, wherein said point level and said ranking is based on any of a positive feedback and a negative feedback received from any of a member of said group of SMEs, said healthcare community member, and said member of said editorial board.

\* \* \* \* \*